US008721711B2

(12) United States Patent
Hanson

(10) Patent No.: US 8,721,711 B2
(45) Date of Patent: May 13, 2014

(54) GRAFT HAVING MICROPOROUS MEMBRANE FOR UNIFORM FLUID INFUSION

(75) Inventor: Stephen R. Hanson, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 492 days.

(21) Appl. No.: 11/765,915

(22) Filed: Jun. 20, 2007

(65) Prior Publication Data

US 2008/0319425 A1 Dec. 25, 2008

(51) Int. Cl.
*A61F 2/06* (2013.01)

(52) U.S. Cl.
USPC .......................................................... 623/1.42

(58) Field of Classification Search
USPC ..................... 623/1.42, 1.43, 1.44, 1.45, 1.46
See application file for complete search history.

(56) References Cited

U.S. PATENT DOCUMENTS

| 3,797,485 | A | | 3/1974 | Urquhart |
|---|---|---|---|---|
| 5,024,671 | A | | 6/1991 | Tu et al. |
| 5,399,352 | A | * | 3/1995 | Hanson .......................... 424/423 |
| 5,405,325 | A | | 4/1995 | Labs |
| 5,405,378 | A | | 4/1995 | Stecker et al. |
| 5,411,550 | A | | 5/1995 | Herweck et al. |
| 5,455,039 | A | | 10/1995 | Edelman et al. |
| 5,523,092 | A | | 6/1996 | Hanson et al. |
| 5,527,532 | A | | 6/1996 | Edelman et al. |
| 5,637,113 | A | | 6/1997 | Tartaglia et al. |
| 5,676,699 | A | | 10/1997 | Gogolewski et al. |
| 5,700,286 | A | | 12/1997 | Tartaglia et al. |
| 5,709,874 | A | | 1/1998 | Hanson et al. |
| 5,795,318 | A | | 8/1998 | Wang et al. |
| 5,800,512 | A | | 9/1998 | Lentz et al. |
| 5,823,989 | A | | 10/1998 | Ostrow |
| 5,824,050 | A | | 10/1998 | Karwoski et al. |

(Continued)

FOREIGN PATENT DOCUMENTS

| EP | 1488761 A1 | 12/2004 |
|---|---|---|
| WO | 2007010295 A1 | 1/2007 |

OTHER PUBLICATIONS

Chen, Changyi et al., "Boundary Layer Infusion of Heparin Prevents Thrombosis and Reduces Neointimal Hyperplasia in Venous Polytetrafluoroethylene Grafts Without Systemic Anticoagulation," J Vasc Surg, 1995, vol. 22, pp. 237-247.
Chen, Changyi et al., "Transgraft Infusion of Heparin to Prevent Early Thrombosis of Expanded PTFE Grafts in Canine Femoral Veins," Ann Vasc Surg, 1996, vol. 10, pp. 147-152.

(Continued)

*Primary Examiner* — Kevin C Sirmons
*Assistant Examiner* — Deanna K Hall
(74) *Attorney, Agent, or Firm* — Scwabe, Williamson & Wyatt

(57) ABSTRACT

Embodiments of the present invention provide a device for the local delivery of a substance into a natural tissue conduit in the mammalian body, having a first element capable of contacting the lumen of the conduit and a second element which overlays first element, a reservoir being formed between the first element and the second element, the interior of the reservoir being capable of fluid communication with the conduit such that a substance placed in the reservoir is delivered into the conduit. In embodiments, the first element may be fully or partially microporous or a separate intermediate microporous membrane may be provided. Also provided are methods of mixing or moving a drug within a reservoir using various mixing elements. Also provided are methods of locally delivering a substance into a natural tissue conduit in the mammalian body utilizing a device in accordance with embodiments of the present invention.

23 Claims, 2 Drawing Sheets

(56) References Cited

U.S. PATENT DOCUMENTS

| | | | |
|---|---|---|---|
| 5,983,134 | A | 11/1999 | Ostrow |
| 5,985,307 | A | 11/1999 | Hanson et al. |
| 6,117,147 | A | 9/2000 | Simpson et al. |
| 6,355,063 | B1 | 3/2002 | Calcote |
| 6,471,689 | B1 * | 10/2002 | Joseph et al. .............. 604/892.1 |
| 6,534,693 | B2 | 3/2003 | Fischell et al. |
| 6,564,093 | B1 | 5/2003 | Ostrow et al. |
| 6,726,923 | B2 | 4/2004 | Iyer et al. |
| 6,776,796 | B2 | 8/2004 | Falotico et al. |
| 6,821,296 | B2 | 11/2004 | Brauckman et al. |
| 6,827,737 | B2 | 12/2004 | Hill et al. |
| 6,869,443 | B2 | 3/2005 | Buscemi et al. |
| 6,981,977 | B2 | 1/2006 | Herweck et al. |
| 7,058,447 | B2 | 6/2006 | Hill et al. |
| 7,351,257 | B2 | 4/2008 | Kaldany |
| 2004/0146546 | A1 | 7/2004 | Gravett et al. |
| 2004/0197409 | A1 | 10/2004 | Iyer et al. |
| 2005/0060020 | A1 | 3/2005 | Jenson |
| 2005/0070989 | A1 * | 3/2005 | Lye et al. ....................... 623/1.4 |
| 2005/0183730 | A1 | 8/2005 | Byrum |
| 2006/0030796 | A1 * | 2/2006 | Xu et al. ........................... 601/2 |
| 2006/0247721 | A1 | 11/2006 | Maschino et al. |
| 2006/0252983 | A1 | 11/2006 | Lembo et al. |
| 2008/0077218 | A1 | 3/2008 | McMorrow et al. |
| 2008/0086198 | A1 | 4/2008 | Owens et al. |
| 2008/0091263 | A1 | 4/2008 | Iyer et al. |

OTHER PUBLICATIONS

Chen, Changyi et al., "Local Infusion of Heparin Reduces Anastomotic Neointimal Hyperplasia in Aortoiliac Expanded Polytetrafluoroethylene Bypass Grafts in Baboons," J Vasc Surg, 2000 vol. 31, pp. 354-363.

Mattar, Samer G. et al., "Local Infusion of FGF-Saporin Reduces Intimal Hyperplasia," Journal of Surgical Research, 1996, vol. 60, pp. 339-344.

Chen, Changyi et al., "Intimal Hyperplasia/Basic Fibroblast Growth Factor: Recombinant Mitotoxin Basic Fibroblast Growth Factor-Saporin Reduces Venous Anastomotic Intimal Hyperplasia in the Arteriovenous Graft," Circulation, 1996, vol. 94, pp. 1989-1995.

Chen, Changyi et al., "Boundary Layer Infusion of Basic Fibroblast Growth Factor Accelerates Intimal Hyperplasia in Endarterectomized Canine Artery," Journal of Surgical Research, 1997, vol. 69, pp. 300-306.

Saavedra, Joseph E. et al., "Localizing Antithrombotic and Vasodilatory Activity with a Novel, Ultrafast Nitric Oxide Donor," J. Med. Chem., 1996, vol. 39, pp. 4361-4365.

Chen, Changyi et al., "Boundary Layer Infusion of Nitric Oxide Reduces Early Smooth Muscle Cell Proliferation in the Endarterectomized Canine Artery," Journal of Surgical Research, 1997, vol. 67, pp. 26-32.

Scott, N. A. et al., "Local Delivery of an Antithrombin Inhibits Platelet-Dependent Thrombosis," Circulation, 1994, vol. 90, pp. 1951-1955.

Markou, Christos P. et al., "A Novel Method for Efficient Drug Delivery," Annals of Biomedical Engineering, 1998, vol. 26, pp. 502-511.

\* cited by examiner

GRAFT HAVING MICROPOROUS MEMBRANE FOR UNIFORM FLUID INFUSION

TECHNICAL FIELD

Embodiments of the present invention relate to devices for the local delivery of a substance into a natural tissue conduit, e.g., a blood vessel, and to methods of therapy utilizing the device. In particular, embodiments of the present invention are directed to devices for delivering substances into a natural tissue conduit in a substantially uniform manner.

BACKGROUND

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ must often be given in amounts dependent upon achieving critical systemic blood levels that may produce devastating side effects in other areas of the body. A prime example of a situation where local therapy is needed with drugs that also produce unwanted systemic side effects is the prevention of complications following the placement of a cardiovascular prosthetic device such as a prosthetic vascular graft or a patch used to repair a damaged vessel.

Graft failure is often associated with the inherent thrombogenicity of the blood contacting surface of the prosthetic device and with the body's own repair mechanisms which may lead to progressive stenotic occlusion due to neointimal fibrosis and hyperplasia. Systemic therapy aimed at preventing coagulation and thrombosis locally at the graft site is often complicated by bleeding that may occur at other sites. Likewise, systemic treatment with growth mediators or chemotherapeutic agents may produce a hyperplastic or hypoplastic response in tissue not specifically targeted. Similarly, the local administration of vasodilators may produce systemic hypotension.

There have been many attempts to render vascular grafts less thrombogenic, e.g., by coating the luminal surface of the graft with non-thrombogenic polymers, cells, or with anticoagulant drugs in a polymer coating. Although some improvements in graft performance have been achieved, complications with clotting, thrombosis, and restenosis, especially due to fibroplasia and smooth muscle proliferation, still abound.

Other attempts to improve graft performance have provided vascular grafts or patches having a tubular drug port attached to a drug reservoir around a macroporous graft. However, such methods do not deliver drugs to the locations in need uniformly, especially when low infusion rates are being utilized.

Therefore, there exists a need for a mechanism for providing local therapy that may deliver drugs substantially uniformly at the site of repair.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1:
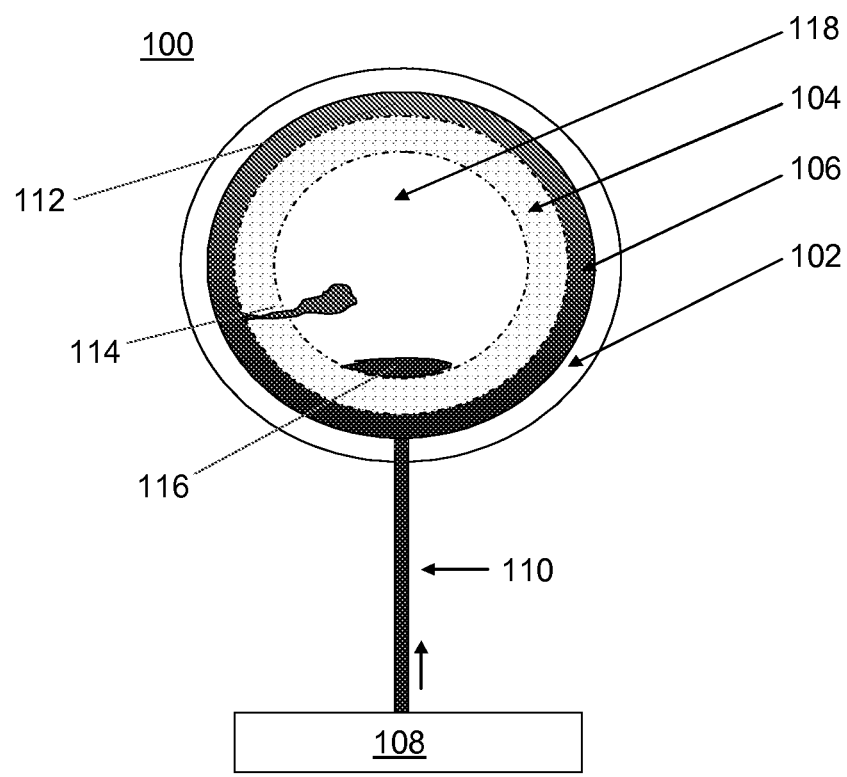
FIG. 1 illustrates a transverse cross-section of a prior art drug delivery device.

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In embodiments, when volume infusion rates are low (e.g. a few ml/month) as contemplated for the delivery of certain drugs, such as Sirolimus, Paclitaxil, or other antiproliferatives, drugs introduced to a natural tissue conduit through the wall of a conventional (e.g., ePTFE) or other porous graft material generally do not enter the conduit in a circumferentially uniform manner. In other words, drugs may be concentrated, for example when drug diffusion across the graft wall is an important component (vs. convective transport of the drug-containing fluid) of drug transport across the graft wall. In this case, a drug may preferentially enter the blood boundary layer at the blood-graft interface at the region nearest to where the catheter from the drug pump (e.g., an osmotic infusion pump) enters the drug reservoir; i.e., the drug is not mixed in the reservoir and may enter the conduit lumen non-uniformly from one side of the reservoir via the shortest diffusion path. Additionally, a drug may be non-uniformly delivered through only a few of the larger holes/pores in the graft by diffusion or convective channeling along pathways of least resistance to flow. Either way, proliferating tissue and/or other local concerns are not targeted optimally. The former problem may be remedied by placing a small mixing device (e.g., a small ball or other element that moves and mixes fluid) within the reservoir itself. The latter problem may be remedied by placing a membrane layer having small pores (microporous) on the outside of the graft between the outer graft surface and the liquid drug reservoir. The microporous membrane layer thus provides the primary resistance to drug transport out of the reservoir and transport only occurs when the reservoir-pump pressure exceeds a threshold, for example the intraluminal pressure of the natural tissue conduit, such as the mean arterial pressure of the treated vessel. The flow of a drug-containing solution through the microporous membrane is controlled and may be specifically regulated for each application/treatment by adjusting the properties of the microporous membrane, the properties of the drug containing solution (e.g., viscosity), and/or the reservoir-pump pressure (in excess of the threshold pressure). When placed over the graft, once a drug is pushed through the rate-limiting microporous membrane, it then easily passes through the larger pore size (lower resistance) layer of the graft. An alternative strategy would be to replace all of or a short length of the graft with a new infusion graft segment having a cuff-reservoir and a microporous membrane.

An embodiment of the present invention provides a device for the local delivery of a substance into a natural tissue conduit in a mammalian body, comprising: a first element comprised of a biocompatible material which may be affixed to the conduit, the first element having a first surface, an opposite second surface, and an intermediate macroporous portion which communicates the second surface with the first surface, wherein the first surface of the macroporous portion is capable of contacting the lumen of the conduit; a second microporous element which overlays the first element; and a third element comprised of a substantially non-porous biocompatible material which overlays the second element, a reservoir having an interior being formed between the third element and the second element, the interior of the reservoir being capable of fluid communication with the conduit via the microporous portion and the macroporous portion such that a substance placed in the reservoir is delivered into the conduit. Such an embodiment may be utilized, for example, to provide local drug delivery into arterial blood flow for prevention or treatment of any disease or condition distal to the site of arterial implantation of the device.

For the purposes of describing embodiments of the present invention, the phrase "natural tissue conduit" refers to any area of a mammalian body which functions to transport substances and includes, but is not limited to, blood vessels of the cardiovascular system (arteries and veins), the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body, etc. Devices in accordance with embodiments of the present invention may be used in any mammal or in any animal in which natural tissue conduits are found.

Embodiments of the present invention also provide a device for the local delivery of a substance into a natural tissue conduit in a mammalian body, wherein the first element further comprises an elongated tubular segment having a substantially non-compliant, hollow body portion which is open at both ends wherein the first surface is the luminal surface of the tubular segment, and wherein the tubular segment is capable of being affixed to the natural tissue conduit at both of the ends of the tubular segment. The first element of the device may consist of any tube, microporous throughout or microporous only through that portion where drug is infused (e.g., microporous only at that portion which communicates with the reservoir and the natural tissue conduit). Either end or both ends of the tubular segment may be designed to be inserted intraluminally, anastomosed surgically, or affixed by mechanical stenting between segments of any natural tissue conduit.

An embodiment of the present invention comprises the device described above wherein the first element forms a tubular prosthesis with the conduit. In an embodiment, the conduit may be a blood vessel and the first element a tubular vascular prosthesis. Alternatively, the first element of the device may comprise a patch which overlies a portion of the conduit. In particular, an embodiment of the present invention provides such a device wherein the conduit is a blood vessel and the first element is a vascular patch. Devices according to embodiments of the invention may be constructed in a variety of sizes such that the inside diameter of the first element is between about 1 mm and 50 mm, thereby allowing the surgeon to select the appropriate size to accommodate a particular vascular application. Basic components of such devices may be found in U.S. Pat. No. 5,399,352, the entire contents of which are hereby incorporated by reference.

Embodiments of the present invention provide a device for local delivery of a drug to a graft site comprised of a vascular graft with a porous portion and a reservoir for the drug overlying the porous portion such that the interior of the reservoir is in fluid communication with the luminal, blood flow contacting surface of the vascular graft via the porous portion through which a drug placed in the reservoir is delivered to the luminal surface of the graft. In addition, embodiments of the present invention provide a vascular patch constructed in like fashion.

An embodiment of the present invention provides tubing attached to and in communication with a drug/fluid reservoir such that the reservoir may be filled or refilled with one or more drugs and/or such that the drug(s) may be changed as therapeutic needs change. Another embodiment of the invention further comprises a pump connected to the tubing to deliver drug to the reservoir and to maintain a desired pressure within the reservoir. In embodiments, a pump may be single use, disposable, reusable, refillable, etc. depending on the desired treatment protocol.

Embodiments of the present invention also provide methods for treating or preventing, including but not limited to, coagulation, thrombus formation, occlusion, fibrosis, intimal hyperplasia, restenosis, inflammation, and infection associated with vascular prosthetic devices.

In an embodiment, there exists a need to provide effective local therapy for treatment of cancer and other diseases in many areas of the body such that the chemotherapy may be localized to targeted tissues, thereby preventing unwanted systemic side effects from systemic administration. Embodiments of the present invention satisfy that need by providing a means to locally deliver a substance into any natural tissue conduit of a body and thereby provide localized therapy to targeted tissues. Alternate embodiments of the invention may be utilized to provide local drug delivery to any conduit, including but not limited to, lymphatic vessels, bile ducts, ureters, the intestinal tract, and the respiratory tree. For example, a transitional cell carcinoma of the bladder may be effectively treated with chemotherapeutic agents by insertion of the device of the present invention into a ureter and administering the appropriate drug.

In an embodiment, a porous portion of a graft may have one or more porous layers. In an embodiment, each of the one or more porous layers may have a number of pores, whether uniform or regular in diameter or shape or non-uniform or irregular. In an embodiment, the pores may be uniformly or regularly distributed throughout the layer, and all the pores may, or a subset thereof may, possess a substantially uniform diameter/cross-section. In an embodiment in which multiple porous layers are utilized, the size(s) of the pores in one layer may differ from the size(s) of the pores in another layer. For example, in an embodiment, an inner layer (closest to the luminal space of the conduit) may have an average pore size that allows easy passage of liquid with drugs solubilized therein, whether solubilized before introduction into the reservoir or while resident in the reservoir. In conjunction with such a large-pore (macroporous) layer, there may be used an overlaid layer that has a much smaller average pore size (microporous) that does not easily allow liquids and drugs contained therein to pass through. Rather, the small pores may be sized specifically to restrict the movement of liquid and drugs contained therein except for in response to a sufficient application of pressure in the surrounding reservoir.

In an alternative embodiment, a single layer having relatively small pores that restrict the movement of drugs solubilized in a liquid carrier vehicle except for in response to a sufficient application of pressure in the surrounding reservoir may be used such that a drug-containing liquid in the reservoir may pass through the small pores directly into the luminal space of the vessel.

For the purposes of describing embodiments of the present invention, the term "macroporous" may be used to describe the pore size of a layer through which solubilized drugs may easily pass. In embodiments, the term macroporous refers to an average pore size (a term which includes an internodal distance as in the case of ePTFE) greater than approximately 10 µm, such as approximately 10 µm to 100 µm.

For the purposes of describing embodiments of the present invention, the term "microporous" may be used to describe the pore size of a layer through which solubilized drugs may be restricted from easy passage without the application of sufficient pressure. A microporous layer blocks all or substantially all movement of a solubilized drug and its carrier liquid across the layer/membrane when the reservoir pressure is below the threshold. Thus, without the application of such pressure, diffusion will not provide for a suitable or desirable amount of movement of a drug through a microporous membrane. In embodiments, the term microporous refers to an average pore size of approximately 10 nm to 10 µm, such as 10 nm to 1000 nm.

In embodiments, the pressure sufficient to cause the movement of a liquid drug through a microporous layer may be a pressure in excess of the intraluminal pressure of the natural tissue conduit, such as the mean arterial blood pressure of the vessel with which the graft is associated.

In an embodiment, a pump attached to a drug/fluid reservoir may introduce drugs into the reservoir at a defined/selected infusion rate and pressure. In an embodiment, a pump attached to a drug/fluid reservoir may introduce drugs into the reservoir at a low infusion rate. At low volume infusion rates, such as used for certain drugs, for example anti-proliferative drugs such as Sirolimus and Paclitaxel, current porous membranes do not utilize a microporous, resistance layer and thus the drugs may pass through macropores near the introductory drug port resulting in a higher concentration of drugs around the one or more pores. For purposes of describing embodiments of the present invention, the phrase "low infusion rate" refers to an infusion rate of less than 1.0 ml/day, such as less than 0.2 ml/day or even less than 0.1 ml/day.

FIG. 1 illustrates a transverse cross-section of a prior art drug delivery device 100. Device 100 has an exterior impermeable cuff 102 surrounding a graft 104 thus forming a reservoir 106 therebetween. A drug pump 108 is coupled to reservoir 106 via catheter 110. As may be seen in FIG. 1, the drug in the prior art device is not uniformly distributed in reservoir 106, but rather is concentrated more at the lower portion of reservoir 106 (see element 112 showing a region of relatively lower concentration of drug within the reservoir). In addition, the drug-containing solution in reservoir 106 passes easily through the larger pores or lower resistance channels (shown with representative pore 114) and results in accumulation (see element 116) of the drug in lumen 118 near the location of the inlet of catheter 110 to reservoir 106.

Figure 2:
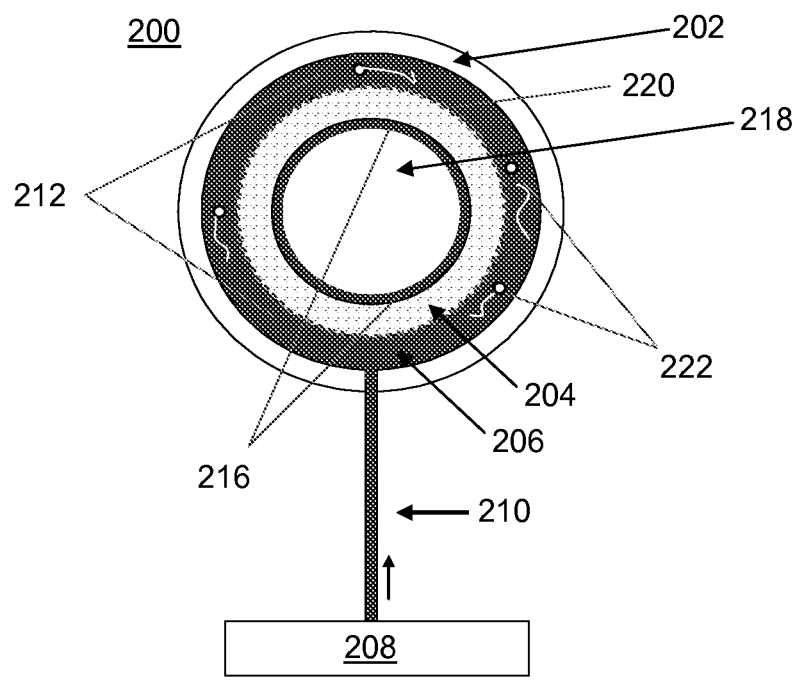
FIG. 2 illustrates a transverse cross-section of a drug delivery device in accordance with various embodiments of the present invention.

By contrast, FIG. 2 illustrates a transverse cross-section of a drug delivery device 200 in accordance with an embodiment of the present invention. Device 200 has an exterior cuff 202 surrounding a graft 204 thus forming a reservoir 206 therebetween. A drug pump 208 is coupled to reservoir 206 via catheter 210. As may be seen in FIG. 2, the drug is uniformly distributed (see element 212) in reservoir 206. In addition, the drug-containing solution in reservoir 206 must pass through the small pores of microporous layer/membrane 220 which provides a resistance barrier between reservoir 206 and graft 204. The resistance function of membrane 220 allows for reservoir 206 to fill or partially fill, and pressure within the reservoir to exceed by some amount a threshold level, prior to the desired movement of drug across membrane 220. Thus, once reservoir 206 is filled or partially filled with a drug-containing solution and the pressure in reservoir 206 increases above a threshold, the drug-containing solution may move across membrane 220 in a relatively uniform manner predominantly by convective mass transport while limiting diffusive transport that may be less uniform around the circumference of the microporous membrane. Drug solution that passes first through microporous layer/membrane 220 may then easily pass through the macroporous pores of graft 204 thus substantially uniformly entering lumen 218 resulting in a substantially uniform infusion of drug (shown with element 216) into lumen 218.

In an embodiment, providing a microporous layer that restricts passage of liquid drugs from the reservoir until a sufficient pressure in the reservoir has been reached allows for the drugs to accumulate in the reservoir to a desired extent, for example filling or partially filling the reservoir, before a suitable pressure gradient is established and drug-containing solutions move across the micoporous layer. In such an embodiment, a more uniform passage of drug solutions through the multiple available pores may be effected thus reducing the extent of isolated concentration of drugs.

In an embodiment, a microporous membrane may allow the reservoir to fill or partially fill, and pressure within the reservoir to exceed by a defined amount a threshold level, prior to substantial movement of drug across the membrane. In an embodiment, the defined amount may be a pressure that provides the desired infusion flow rate.

FIG. 2 also illustrates a further embodiment of the invention in which one or more mixing elements 222 are provided.

Mixing elements 222 may be provided to assist with mixing and/or distributing the drug(s) in reservoir 206. Mixing elements 222 may be freely movable within reservoir 206 or may be secured to at least a portion of cuff 202 and/or membrane 220.

In an embodiment, upon initial use of a graft, the reservoir may be prefilled with a drug to ensure that uniform drug delivery may be established in a short period of time. Alternatively, in some situations it may be desired to delay the infusion of drugs into a vessel during the first postoperative day or few days to allow some initial healing or other biological responses to occur. In such an embodiment, the drug reservoir may be empty or only partially filled (or filled with an inactive solution such as saline) to delay the infusion of drug into the vessel until the desired time for first delivery.

In an embodiment in which a low volume infusion rate is utilized, the pressure gradient needed to move a drug across the microporous layer may take one or more days to achieve thus delaying the first introduction of the drug into the vessel. However, in embodiments, the delay may be addressed as discussed above, or in other embodiments, may be a useful/desired outcome.

In an embodiment, as described above, a microporous layer may be in direct blood contact with the luminal space of the conduit (such as a blood vessel) or may overlay a macroporous layer. In an embodiment in which a microporous layer overlays a macroporous layer, when the reservoir pressure causes the movement of a drug uniformly or substantially uniformly across the microporous layer, the drug enters a space between the microporous layer and the macroporous layer. At such a time, the drug has thus been delivered to the space between the layers in a relatively uniform manner and may then easily pass through the macroporous layer and into the luminal space of the conduit in a more uniform manner than without the use of the overlayed microporous layer.

In an embodiment, a drug may move from a reservoir across a microporous layer in a uniform or substantially uniform circumferential manner. In such an embodiment, the drug may be delivered to the lumen of the conduit from all directions thus ensuring delivery of the drug to the entire conduit, not just an isolated portion thereof. More uniform delivery of a drug provides a safer mechanism for delivering drugs to a conduit (such as a blood vessel) as the amount of drug that is being delivered may be reduced because the delivery is more targeted and effective. In addition, more effective delivery of the drug means that there will likely be reduced side effects to the patient. Also, more effective delivery means that less drug need be used and the drug pump (which may or may not be refillable) will last longer before needing to be replaced or refilled thus increasing patient satisfaction and reducing costs.

Figure 3:
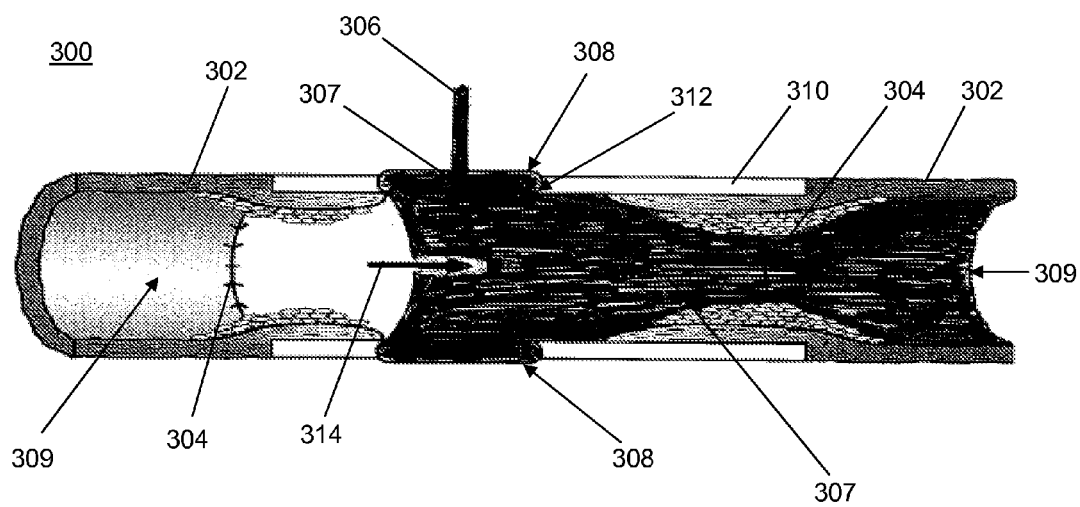
FIG. 3 illustrates a longitudinal cross-section of a drug delivery device in place in a tissue conduit in accordance with various embodiments of the present invention.

FIG. 3 illustrates a longitudinal cross-section of a drug delivery device 300 in place in a tissue conduit 302 in accordance with various embodiments of the present invention. Drug delivery device 300 has been anastomosed to tissue conduit 302 as shown by sutures 304. Drug delivery device 300 shows a drug inlet/catheter 306 introducing a drug 307 into a reservoir 308 that extends circumferentially around lumen 309 of tissue conduit 302. In the illustrated embodiment, reservoir 308 is shown as a portion of graft 310, in other words, a portion of graft 310 has been replaced. Reservoir 308 is separated from lumen 309 of tissue conduit 302 by a microporous layer/membrane 312. As illustrated in FIG. 3, the pressure in reservoir 308 is above the mean arterial vessel pressure by a desired amount to cause drug 307 to flow across microporous membrane 312 at a desired rate. In embodiments, due to the movement of blood (as shown by arrow 314), drug 307 tends to be concentrated toward the outer perimeter of lumen 309, which is beneficial for delivering drugs locally to tissues near the site of drug delivery, as opposed to much further downstream.

In an alternative embodiment, the microporous layer and/or the macroporous layer may be provided with pores in a designed configuration or in one or more specified locations to direct the drug to one or more desired portions of the vessel.

In an embodiment, the pores of the various layers may cover the entire length of the graft, or may only be present in a portion of the graft. In an embodiment, it may be desired to provide a drug close to the upstream end of the graft, for example to provide an anticoagulant, or close to the downstream end of the graft, for example to treat tissue proliferation. In certain situations, the downstream end of the graft may be the primary location of restenosis and tissue proliferation, thus addressing at least the downstream end of the graft may be sufficient, in embodiments, to provide a positive result.

In an embodiment, a plurality of drug infusion ports may be utilized at different locations along the graft. For example, in an embodiment, a first drug infusion port may be close to the upstream end of the graft and may be used to deliver an anticoagulant and a second drug infusion port may be close to the downstream end of the graft and may be used to deliver an antiproliferative drug. In such an embodiment, the reservoir and/or the space between the layers (if multiple layers are utilized) may be divided to avoid mixing of the drugs, or, since mixing of the drugs is generally not problematic, no division or separation may be needed.

In an embodiment in which multiple infusion ports are present, each infusion port may be provided with a separate pump so that separate control over the rate of infusion may be provided. In an alternative embodiment, a single pump may be used with multiple outlets, whether having single or multiple simultaneous settings for the various infusion rates.

In an embodiment, any of the major spaces, such as the reservoir, in which a drug is held prior to delivery to a conduit may be provided with one or more mixing elements to assist with distributing the fluid around the reservoir. An example of such mixing elements is provided in FIG. 2. In an embodiment, such mixing elements may be small beads made of, for example Teflon. In an embodiment, the beads may be made of a magnetic material, such as iron, the movement of which may be controlled by application of an external magnetic force. In an embodiment, a magnetic material may be further coated by a plastic or a non-stick material such as Teflon. In embodiments, the beads or other mixing elements may be free flowing within the reservoir or other space, or may be partially secured to a portion of the graft. In an embodiment, the beads may be spherical or non-spherical, and may be solid, or may have one or more holes or openings therein.

In an embodiment, a graft or a portion thereof may be constructed from any biocompatible materials such as polymers, metals or ceramics, for example ePTFE, Teflon (polytetrafluoroethylene), knitted or woven Dacron (polyethylene terephthalate), etc. In an embodiment, one or more surfaces of a device may further comprise a coating on a portion of the surface, for example a surface in contact with the lumen of the conduit, to improve biocompatibility. For example, a surface may be coated with a polymer selected from the group including, but not limited to, fluorocarbon, hydrocarbon, silicone rubber and polyurethane based polymers.

In an embodiment, the tubing and/or pump may be constructed from any biocompatible material, including but not restricted to, silicone rubber, polyurethanes, fluorocarbon polymers, polyethylene, polyvinylchloride or other polymers. In an embodiment, a drug source and/or a pump connected to the tubing may be external or internal, e.g., implanted.

As contemplated in embodiments of the present invention, the substance in the reservoir may be any substance, including any drug, and the device may be used for local delivery of such substances to prevent or treat a variety of disease syndromes or to promote or enhance desired activity within the body.

In an embodiment, a substance may be a drug in solution. In an embodiment, a substance may be a drug initially in solid form resident in or introduced into the reservoir, to which a liquid solubilizing agent may be later added in the reservoir prior to delivery of the solubilized drug. Alternatively, no solubilizing agent may be electively added. In such an embodiment, the drug may be solubilized on contact with aqueous blood that penetrates the macroporous and/or microporous membrane(s), and then the solubilized drug may diffuse through those membranes into the lumenal flowing blood. In such an embodiment, a pump may not be needed to move the drug into the tissue conduit as the primary mode of transport of the drug is effected by diffusion.

In an embodiment, a substance such as an anticoagulant, including but not limited to, heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FBI, FIX, FVIII, FV, FVII and tissue factor may be delivered.

Another embodiment of the present invention provides a device described herein wherein the substance in the reservoir inhibits platelet deposition and thrombus formation or promotes thrombolysis and thrombus dissolution. Examples of such substances include, but are not limited to, plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors; antagonists of glycoprotein receptors including (GP) Ib,GP IIb/IIIa, antagonists of collagen receptors, and antagonists of platelet thrombin receptors.

Another embodiment provides a device described herein wherein the substance in the reservoir is an antiproliferative compound such as Sirolimus or Paclitaxel.

An alternative embodiment provides a device described herein wherein the substance in the reservoir affects platelet metabolic function. Examples of such substances include, but are not limited to, prostaglandins, cyclooxygenase inhibitors, phosphodiesterase or thromboxane synthetase inhibitors, inhibitors of calcium transport, or elevators of cyclic adenosine monophosphate (cyclic AMP).

Still another embodiment of the present invention provides a device described herein wherein the substance in the reservoir prevents restenosis of a blood vessel. Examples of such substances include, but are not limited to, a growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, and bifunctional molecules comprising an antibody and a cytotoxin.

In an embodiment, the substance in the device of the present invention may also be a vasodilator, such as nitroglycerin, nitroprusside or other nitric oxide liberators. The vasodilator may also include other suitable vasoactive agents such as beta receptor blocking drugs, inhibitors of intra-cellular calcium transport; prostaglandins, thromboxane antagonists, and the like.

An embodiment of the present invention further provides a method of locally delivering a substance into a natural tissue conduit in a mammalian body, comprising the steps of: forming a device comprising a first element comprised of a biocompatible material which may be affixed to the conduit having a first surface, an opposite second surface, and an intermediate macroporous portion which communicates the second surface with the first surface, wherein the first surface of the macroporous portion is capable of contacting the lumen of the conduit, and a second microporous portion which overlays the second surface of the first element; and a third element comprised of a substantially non-porous biocompatible material which overlays the second element, a reservoir having an interior being formed between the third element and the second element, the interior of the reservoir being capable of fluid communication with the conduit via the macroporous portion and the microporous portion such that a substance placed in the reservoir is delivered into the conduit; placing a substance in the reservoir; and affixing the device to the natural tissue conduit such that the first surface of the macroporous portion contacts the lumen of the conduit and such that the interior of the reservoir is in fluid communication with the conduit via the microporous portion of the second element and the macroporous portion of the first element.

An embodiment of the present invention also provides a method of locally delivering a substance into a natural tissue conduit in a mammalian body, comprising affixing to a natural tissue conduit a device comprising a first element comprised of a biocompatible material which may be affixed to the conduit having a first surface, an opposite second surface, and an intermediate microporous portion which communicates the second surface with the first surface, wherein the first surface of the microporous portion is capable of contacting the lumen of the conduit, and a second element comprised of a substantially non-porous biocompatible material which overlays the second surface of the first element, a reservoir being formed between the first element and the second element, the interior of the reservoir being capable of fluid communication with the conduit via the microporous portion such that a substance placed in the reservoir is delivered into the conduit.

Utilizing methods for predicting downstream concentration of substances (administered by methods and devices in accordance with embodiments of the present invention), for example as taught in U.S. Pat. No. 5,399,352, the entire contents of which are hereby incorporated by reference, one skilled in the art may determine suitable dosage requirements and treatment regimens for any substance placed in the reservoir of the device. Dosages and regimens will vary, of course, depending upon the tissue targeted for therapy and upon the particular drug utilized. In embodiments, the substances described herein may be utilized in the methods for local drug delivery taught herein in amounts determined by other optimization procedures known in the art.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways.

This application is intended to cover any adaptations or variations of the embodiments discussed herein. Therefore, it is manifestly intended that embodiments in accordance with the present invention be limited only by the claims and the equivalents thereof.

What is claimed is:

1. A device for the local delivery of a drug-containing solution into a natural tissue conduit in a mammalian body, comprising:
    a prosthetic graft configured to be affixed to the natural tissue conduit to provide a lumen connecting at least two segments of the natural tissue conduit, the prosthetic graft comprising a reservoir comprising a microporous membrane, the microporous membrane being microporous relative to a drug-containing solution; and
    a pump provided to introduce the drug-containing solution to the reservoir at an infusion rate no greater than 1.0 ml/day and produce a threshold pressure within the reservoir, wherein the microporous membrane has a porosity to restrain the drug-containing solution within the reservoir and release the drug-containing solution from the reservoir to bloodstream in the lumen of the prosthetic graft upon application of the threshold pressure, wherein the microporous membrane releases the drug-containing solution locally and substantially uniformly around an internal circumference of the prosthetic graft lumen and thereby to at least one of the at least two segments of the natural tissue conduit.

2. The device of claim 1, further comprising a macroporous portion configured to be between the microporous membrane and the lumen of the prosthetic graft.

3. The device of claim 1, wherein the microporous membrane is provided only at the portion of the prosthetic graft where the drug-containing solution is to be delivered to the lumen of the prosthetic graft.

4. The device of claim 1, wherein the microporous membrane comprises PTFE.

5. The device of claim 1, further comprising a catheter attached at a first end to the reservoir and at a second end to the pump.

6. The device of claim 1, wherein the drug-containing solution can be added or changed at the pump.

7. The device of claim 1, wherein the drug-containing solution comprises at least one of sirolimus and paclitaxel.

8. The device of claim 1, wherein the drug-containing solution comprises a drug selected from the group consisting of anti-proliferatives, anti-thrombogenics, anti-inflammatories, antibiotics, cancer treatment drugs, anti-restenosis drugs, anti-platelet drugs, vasodilators, anticoagulants, and chemotherapy drugs.

9. The device of claim 1, wherein the natural tissue conduit comprises tissue selected from the group consisting of blood vessels, port-caval system, lymphatic tissue, bile ducts, ureters, intestinal tract, respiratory tissue, and endocrine system.

10. The device of claim 1, wherein the microporous membrane comprises pores having an average pore size of approximately 10 nm to 1000 nm.

11. The device of claim 2, wherein the macroporous element has pores having an average pore size or internodal distance greater than approximately 10 μm.

12. The device of claim 1, further comprising one or more mixing elements disposed within the reservoir.

13. The device of claim 12, wherein the one or more mixing elements are beads.

14. The device of claim 12, wherein the one or more mixing elements comprise a nonstick material or a magnetic material.

15. A device for local drug delivery, comprising:
    a vascular graft configured to connect at least two segments of blood vessel and provide a lumen therebetween, the vascular graft comprising a reservoir comprising a microporous membrane, wherein the microporous membrane has a porosity to restrain a drug-containing solution within the reservoir and release the drug-containing solution from the reservoir into bloodstream in the lumen of the vascular graft when a threshold pressure within the reservoir is achieved, wherein the microporous membrane releases the drug-containing solution locally and substantially uniformly around an internal circumference of the vascular graft lumen and thereby to at least one of the at least two segments of blood vessel; and
    an implanted pump connected to the reservoir by a catheter, the pump providing the drug-containing solution to the reservoir at an infusion rate of no more than about 1.0 ml/day and supplying the threshold pressure within the reservoir, wherein the pump is configured to be refillable with the drug-containing solution.

16. The device of claim 15, wherein the microporous membrane has pores having an average pore size of approximately 10 nm to 1000 nm.

17. The device of claim 15, further comprising one or more mixing elements disposed within the reservoir.

18. A method of forming a device for locally and uniformly delivering a drug-containing solution into a natural tissue conduit in a mammalian body, comprising:
    providing a prosthetic graft configured to be affixed to a natural tissue conduit, the prosthetic graft having a lumen configured to connect at least two segments of the natural tissue conduit;
    providing a reservoir over the prosthetic graft, the reservoir comprising a microporous membrane,
    the microporous membrane having a porosity to restrain the drug-containing solution within the reservoir and release the drug-containing solution from the reservoir into the lumen of the prosthetic graft when a threshold pressure within the reservoir is achieved, the microporous membrane locally and substantially uniformly releasing the drug-containing solution around an internal circumference of the prosthetic graft lumen;
    affixing a catheter to the reservoir; and
    connecting a pump to the catheter so that the pump can provide the drug-containing solution to the reservoir via the catheter at an infusion rate no greater than 1.0 ml/day and provide the threshold pressure to the reservoir.

19. The method of claim 18, further comprising providing at least one mixing element within the reservoir.

20. The method of claim 18, wherein the porosity of the microporous membrane, the viscosity of the drug-containing solution, and the pressure provided to the reservoir by the pump are configured to provide an anti-proliferative drug to a blood vessel in a local and substantially uniform manner.

21. A method of locally and substantially uniformly delivering a drug to a natural tissue conduit tissue of a mammal, comprising:
    affixing a prosthetic graft to and between at least two segments of blood vessel, the prosthetic graft comprising:
        an exterior cuff, the exterior cuff being substantially non-porous to a drug-containing solution; and
        a microporous membrane that, with the exterior cuff, forms a reservoir, wherein the microporous membrane has a porosity to restrict movement of the drug-containing solution from the reservoir and release the drug-containing solution from the reservoir into bloodstream in a lumen of the prosthetic graft when a threshold pressure within the reservoir is achieved, wherein responsive to the threshold pressure the microporous membrane locally and substantially uniformly releases the drug-containing solution into the prosthetic graft lumen around an internal circumference thereof;

affixing a pump to the reservoir via a catheter;

providing the drug-containing solution within the pump;

providing the drug-containing solution to the reservoir at an infusion rate of no greater than about 1.0 ml/day via the pump and catheter; and providing the threshold pressure to the reservoir.

22. The method of claim 21, wherein the drug-containing solution comprises a drug selected from the group consisting of anti-proliferatives, anti-thrombogenics, anti-inflammatories, antibiotics, cancer treatment drugs, anti-restenosis drugs, anti-platelet drugs, vasodilators, anticoagulants, and chemotherapy drugs.

23. The method of claim 21, wherein the pump is implanted in the mammal and is refillable with the drug-containing solution.

* * * * *